United States Patent
Janajreh et al.

(10) Patent No.: US 10,786,801 B2
(45) Date of Patent: Sep. 29, 2020

(54) CONTINUOUS SONO-CHEMICAL REACTORS AND METHODS OF USING THE SAME

(71) Applicant: Khalifa University of Science and Technology, Abu Dhabi (AE)

(72) Inventors: Isam Janajreh, Abu Dhabi (AE); Mohammed Noorul Hussain, Abu Dhabi (AE); Tala El Samad, Abu Dhabi (AE); Fadi Ataya, Abu Dhabi (AE)

(73) Assignee: KHALIFA UNIVERSITY OF SCIENCE AND TECHNOLOGY, Abu Dhabi (AE)

( * ) Notice: Subject to any disclaimer, the term of this patent is extended or adjusted under 35 U.S.C. 154(b) by 0 days.

(21) Appl. No.: 16/462,720

(22) PCT Filed: Nov. 21, 2017

(86) PCT No.: PCT/US2017/062664
§ 371 (c)(1),
(2) Date: May 21, 2019

(87) PCT Pub. No.: WO2018/098097
PCT Pub. Date: May 31, 2018

(65) Prior Publication Data
US 2019/0366297 A1 Dec. 5, 2019

Related U.S. Application Data

(60) Provisional application No. 62/425,090, filed on Nov. 22, 2016.

(51) Int. Cl.
*B01J 19/10* (2006.01)
*C07C 67/02* (2006.01)
(Continued)

(52) U.S. Cl.
CPC .............. *B01J 19/10* (2013.01); *B01J 14/00* (2013.01); *B01J 19/006* (2013.01); *B01J 19/008* (2013.01);
(Continued)

(58) Field of Classification Search
USPC .................................................. 422/127, 128
See application file for complete search history.

(56) References Cited

U.S. PATENT DOCUMENTS

| 5,658,534 A | 8/1997 | Desborough et al. |
| 6,884,900 B2 * | 4/2005 | Maeda ..................... B01J 19/10 554/169 |

(Continued)

FOREIGN PATENT DOCUMENTS

| CN | 203803395 U | 9/2014 |
| CN | 105363405 A | 3/2016 |

(Continued)

OTHER PUBLICATIONS

Derwent Abstract for WO 2014119982 A1 (Aug. 2014). (Year: 2014).*
Machine translation for DE 865832 C (Feb. 1953). Retrieved from Espacenet website on Jan. 30, 2020. (Year: 2020).*

*Primary Examiner* — Jennifer A Leung
(74) *Attorney, Agent, or Firm* — Hayes Soloway PC (57) ABSTRACT

Sono-chemical reactors and methods of using the same are provided. The sono-chemical reactors may include a plurality of sections that are sequentially connected along a longitudinal direction of the sono-chemical reactor. The plurality of sections may include a sono-reactor section that includes a reactant inlet through which reactants are supplied into the sono-reactor section and a static mixer section that is configured to receive a first reactant/product mixture from the sono-reactor section and is configured mix the first reactant/product mixture therein for reaction between unre- (Continued)

acted reactants. An inner space of the sono-reactor section may taper along the longitudinal direction of the chemical reactor away from the reactant inlet. The plurality of sections may also include a product separation section that is configured to receive a second reactant/product mixture from the static mixer section and is configured to separate a product from the second reactant/product mixture.

14 Claims, 9 Drawing Sheets

(51) Int. Cl.
  *B01J 14/00* (2006.01)
  *B01J 19/00* (2006.01)
  *C10L 1/02* (2006.01)
(52) U.S. Cl.
  CPC .............. *C07C 67/02* (2013.01); *C10L 1/02* (2013.01); *B01J 2219/00166* (2013.01); *B01J 2219/00772* (2013.01); *B01J 2219/00774* (2013.01); *B01J 2219/185* (2013.01); *C10L 2290/34* (2013.01); *C10L 2290/565* (2013.01)

(56) References Cited

U.S. PATENT DOCUMENTS

| | | | |
|---|---|---|---|
| 6,957,805 B2 * | 10/2005 | Ehrlicher | B29B 7/7414 |
| | | | 261/81 |
| 7,160,516 B2 | 1/2007 | Simon et al. | |
| 7,846,341 B2 | 12/2010 | Babaev | |
| 2005/0027137 A1 * | 2/2005 | Hooker | B01J 4/02 |
| | | | 554/176 |
| 2006/0050605 A1 | 3/2006 | Markhasim | |
| 2008/0251375 A1 | 10/2008 | Hielscher et al. | |
| 2015/0367313 A1 | 12/2015 | Kozyuk | |

FOREIGN PATENT DOCUMENTS

| | | | |
|---|---|---|---|
| DE | 865832 C * | 2/1953 | ......... B01F 11/0241 |
| KR | 1020090118275 A | 11/2009 | |
| WO | WO-2014119982 A1 * | 8/2014 | ............ B01J 19/008 |

* cited by examiner

CONTINUOUS SONO-CHEMICAL REACTORS AND METHODS OF USING THE SAME

RELATED APPLICATION

This application claims the benefit of U.S. Provisional Patent Application Ser. No. 62/425,090, filed on Nov. 22, 2016, the disclosure of which is incorporated by reference herein in its entirety.

FIELD OF THE INVENTION

The present invention generally relates to reactors and methods of using the reactors and, more particularly, to continuous sono-chemical reactors and methods of producing biodiesel using the continuous sono-chemical reactors.

BACKGROUND

Biodiesel production by the transesterification reaction may be a slow process owing to the nature of the reaction. Ultrasound may generate millions of micro level cavitation bubbles, which cause tremendous increase in mass transfer upon implosion. This phenomenon may increase the reaction rate in a localized zone by several orders of magnitude. Accordingly, various reactors using this phenomenon have been developed as discussed in, for example, U.S. Pat. Nos. 5,658,534; 7,160,516 and 7,846,341 and US Patent Application Publication Nos. 2006/0050605 and 2015/0367313. The use of ultrasonic processors for biodiesel production has been proposed; however, compact, inexpensive, and simple reactors are still commercially unavailable. Developing simple and small reactors may be beneficial since those can be installed near any potential source, such as vegetable/animal oil, waste cooking oil (WCO) including small residential community, restaurants, and the treated tallow of slaughter house.

For sonicating flowing fluid, special sonication devices such as ultrasonic flow cells have been developed but these are only capable of processing limited volumes of fluid. Increasing volume of fluid may require high power ultrasound devices, which may be undesirable, as an increase in power consumption has negative effects in both economic and environmental terms. Therefore, developing continuous and short processing reactors that may allow reactant mixtures to flow while sonicating those may be beneficial.

SUMMARY OF THE INVENTION

According to some embodiments of the present invention, sono-chemical reactors may include a plurality of sections that are sequentially connected along a longitudinal direction of the sono-chemical reactor. The plurality of sections may include a sono-reactor section that includes a reactant inlet through which reactants are supplied into the sono-reactor section and a static mixer section that is configured to receive a first reactant/product mixture from the sono-reactor section and is configured mix the first reactant/product mixture therein for reaction between unreacted reactants. An inner space of the sono-reactor section may taper along the longitudinal direction of the sono-chemical reactor away from the reactant inlet.

In some embodiments, the plurality of sections may also include a product separation section that is configured to receive a second reactant/product mixture from the static mixer section and is configured to separate a product from the second reactant/product mixture. In some embodiments, an inner space of the product separation section may taper along the longitudinal direction of the sono-chemical reactor away from the static mixer section.

According to some embodiments of the present invention, methods of producing biodiesel may be performed using the sono-chemical reactors. The methods may include continuously supplying the reactants into the sono-chemical reactor and discharging a product from the sono-chemical reactor.

BRIEF DESCRIPTION OF THE DRAWINGS

FIGS. 4A, 4B, and 4C are cross-sectional views

DETAILED DESCRIPTION

As used herein the term "and/or" includes any and all combinations of one or more of the associated listed items. Like reference numbers refer to like elements throughout. It will be understood that the term "simultaneous" and "concurrent" means at approximately the same time but not necessarily exactly the same time.

According to some embodiments of the present invention, continuous sono-chemical reactors are provided. In some embodiments, the reactors may be used for transesterification of waste oil. The reactors may include multiple stages (e.g., three stages) and reactants and/or products may continuously flow through those stages. Accordingly, the residence time of the reactants and/or products may be reduced, and, when the reactors are used for transesterification of waste oil, the cost of the transesterification process into glycerin and fatty acid methyl esters may be decreased. In some embodiments, the reactors may be formed of steel, aluminum, and/or materials having durability similar to steel and aluminum.

Figure 1:
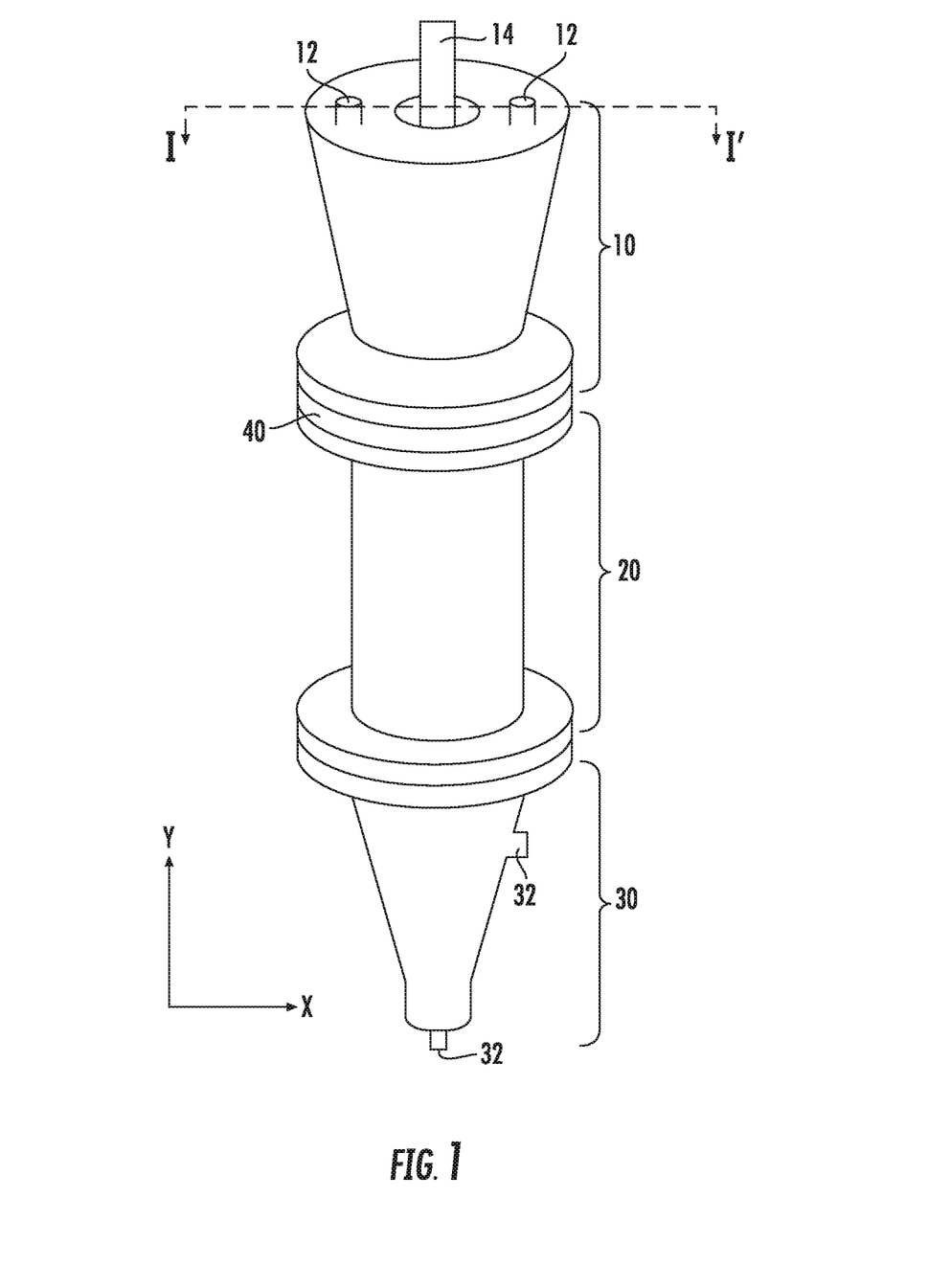
FIG. 1 is a perspective view of a sono-chemical reactor according to some embodiments of the present invention.
Figure 2:
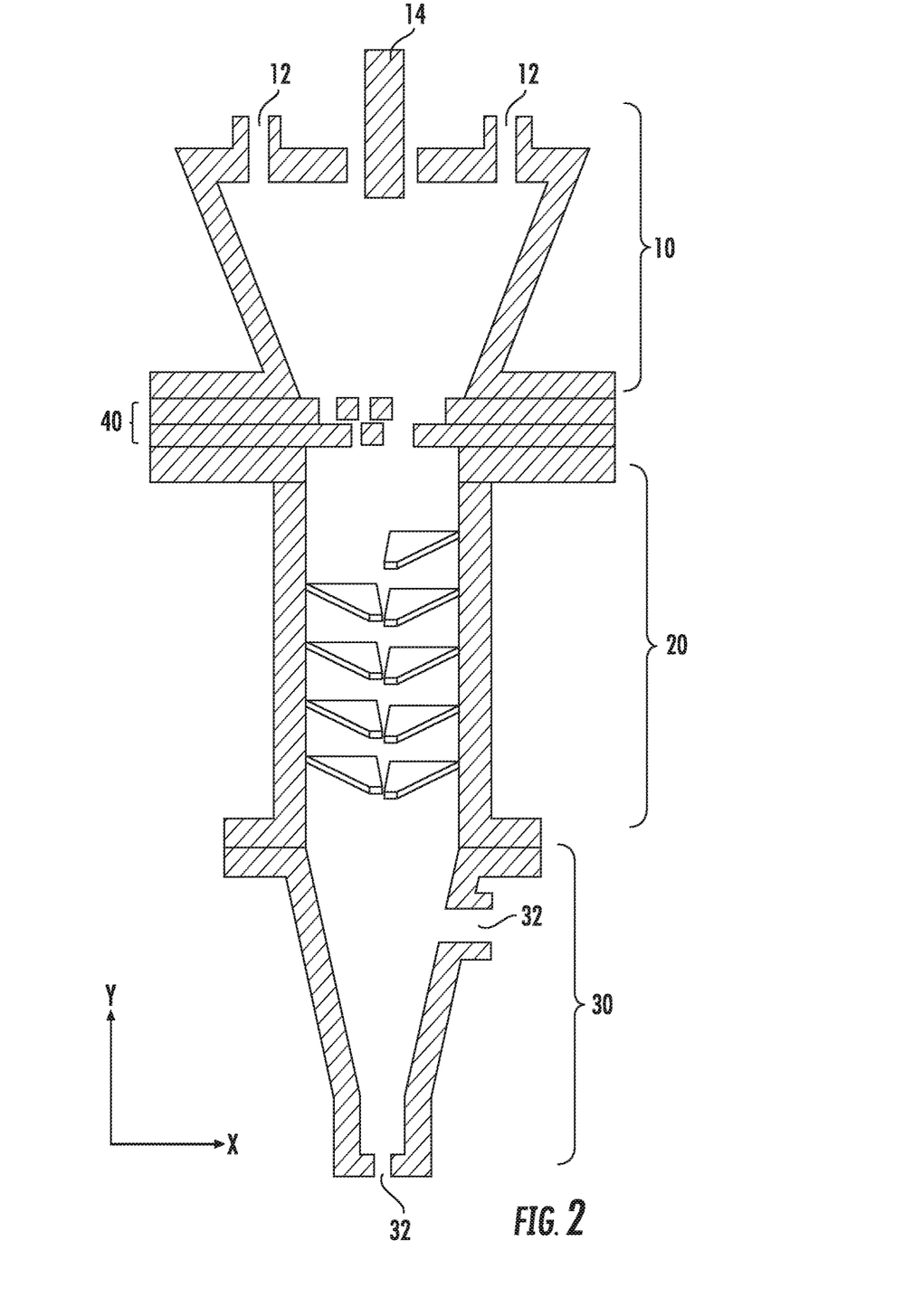
FIG. 2 is a cross-sectional view taken along the line I-I' of FIG. 1 according to some embodiments of the present invention.

FIG. 1 is a perspective view of a sono-chemical reactor according to some embodiments of the present invention, and FIG. 2 is a cross-sectional view taken along the line I-I' of FIG. 1 according to some embodiments of the present invention. Referring to FIG. 1, a sono-chemical reactor may include multiple sections sequentially connected to each other along a longitudinal direction of the sono-chemical reactor (e.g., Y direction of FIG. 1). In some embodiments, multiple sections of the sono-chemical reactor may be vertically stacked. The sono-chemical reactor may include a sono-reactor section 10 in which at least a portion of a sonotrode 14 is disposed. For example, the sono-reactor section 10 has a length in the Y direction of about 10 cm.

In some embodiments, the sono-reactor section 10 may have a converging housing as illustrated in FIG. 1 and may include inlets 12 in a top surface of the sono-reactor section 10. Although FIG. 1 shows two inlets 12, it will be understood that a single inlet or more than two inlets can be included in the sono-reactor section 10. In some embodiments, an inner space of the sono-reactor section 10 may taper along the longitudinal direction of the sono-chemical reactor away from the top surface of the sono-reactor section 10. The tapering inner space of the sono-reactor section 10 may facilitate acoustic energy concentration and may make the sono-reactor section 10 operate like a pseudo ultrasonic flow cell. Accordingly, the sono-reactor section 10 may provide higher energy per unit volume than conventional cylinder-shape rectors, and a sonotrode of any size may be used.

In some embodiments, waste oils may be supplied into the sono-reactor section 10 through the inlets 12 and may be converted into glycerin and fatty acid methyl esters in the presence of alcohol. For example, methanol ($CH_3OH$) and/or ethanol ($C_2H_5OH$) may be used.

In some embodiments, a catalyst may be added to the sono-reactor section 10 through the inlets 12 to increase reaction rates. The catalyst may include, for example, sodium hydroxide (NaOH) and/or potassium hydroxide (KOH), and other catalysts used in the transesterification of oils may be used. Two or more inlets 12 may allow simultaneous or concurrent addition of the waste oil, alcohol and catalyst to the sono-reactor section 10.

The sono-chemical reactor may include a static mixer section 20 including a static mixer therein and may have a cylindrical shape. The static mixer section 20 may be configured to receive a first reactant/product mixture (e.g., a mixture of unreacted waste oil and alcohol, glycerin and fatty acid methyl esters) and may be configured mix the first reactant/product mixture for reaction between unreacted reactants using the static mixer. Conversion of any unreacted reactants into products (e.g., conversion of unreacted waste oil and alcohol into glycerin and fatty acid methyl esters) using static, geometrical mixing may be a slower constrained reaction. For example, the static mixer section 20 has a length in the Y direction of about 15 cm.

In some embodiments, the static mixer of the static mixer section 20 may be conventional helical screw type or innovative staggered desiccated type. In some embodiments, the static mixer of the static mixer section 20 may include a series of blades, and the blades may have any shapes and/or sizes depending on the viscosity of the fluid. In some embodiments, the blades may include a helical channel, circular ladder or simple staggered chevrons design and may be formed of any chemically inert and soft materials, such as plastic or a harder metal (e.g., mild steel and alloys).

Still referring to FIG. 2, in some embodiments, an inner space of the static mixer section 20 may have a substantially uniform diameter along the longitudinal direction of the sono-chemical reactor. The diameter of the inner space of the static mixer section 20 may be substantially equal to a smallest diameter of the inner space of the sono-reactor section 10. As illustrated in FIG. 2, in some embodiments, the inner space of the sono-reactor section 10 may have the smallest diameter adjacent the static mixer section 20.

In some embodiments, the sono-chemical reactor may further include a product separation section 30 that is configured to receive a second reactant/product mixture from the static mixer section 20 and is configured to separate products (e.g., biodiesel) from byproducts (e.g., glycerol). The product separation section 30 may include multiple outlets 32, and, in some embodiments, one of the outlets 32 may be near the top of the product separation section 30 to draw off the lighter biodiesel, and one of the outlets 32 may be located at the bottom of product separation section 30 to draw off the heavier glycerol, as illustrated in FIGS. 1 and 2. In some embodiments, one or more outlets 32 are a free flow type that may be connected to a secondary peristaltic pump and may be used to discharge biodiesel and/or glycerin. For example, the product separation section 30 has a length in the Y direction of about 13 cm.

Referring to FIG. 2, an inner space of the product separation section 30 may taper along the longitudinal direction of the sono-chemical reactor away from the static mixer section 20. It will be understood that the tapering inner space of the product separation section 30 may promote phase separation between products and byproducts.

In some embodiments, the sono-chemical reactor may also include a controlling disk section 40 including multiple controlling disks between the sono-reactor section 10 and the static mixer section 20. The controlling disk section 40 may be configured to control flow of fluid from the sono-reactor section 10 to the static mixer section 20.

The sono-chemical reactors according to some embodiments of the present invention may be used for the transesterification reaction for biodiesel production from vegetable oils or waste cooking oils (WCO), however, the present invention is not limited thereto. Reactions with reactants whose properties are similar to vegetable oil may be processed using the sono-chemical reactors according to some embodiments of the present invention. The size of the sono-chemical reactors may be kept compact to avoid increasing the number of sonotrodes and to concentrate the sonic energy. The metallic material can be used for an housing of the sono-chemical reactors, and, for example, steel and/or aluminum may be used. In some embodiments, other materials having durability similar to steel and aluminum may be used.

The static mixer section 20 may further process unreacted reactants passively by non-energy consuming conversion process. The static mixer section 20 may maximize usage of space of the sono-chemical reactors. The size and shapes of the static mixer of the static mixer section 20 may vary depending upon use, viscosity and velocity of reactants.

In some embodiments, separation and discharging products and/or byproducts may be performed concurrently in the product separation section 30. Since the product separation section 30 may continuously discharge byproducts, a reverse reaction may be reduced or possibly inhibited such that conversion of reactants and/or yield of products may increase or possibly maximized.

The transesterification reaction for biodiesel production may be described as shown in Equation (1). Starting with either vegetable oils or waste cooking oils, alcohol is added to produce Fatty Acid Methyl Ester (FAME) and glycerol.

$$\text{Triglyceride (oil)} + 3 \text{ Alcohol} \rightleftarrows 3 \text{ FAME} + \text{Glycerol} \qquad (1)$$

Figure 3:
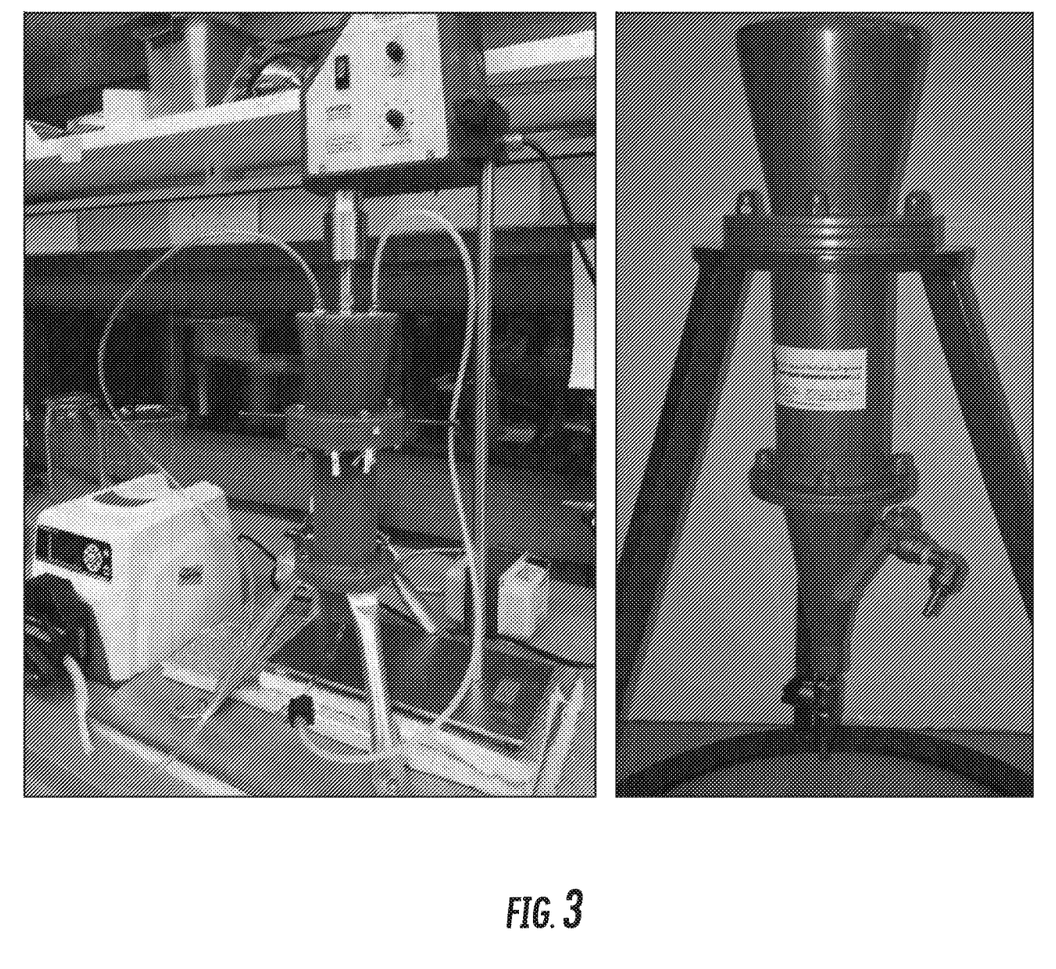
FIG. 3 is a digital image of two prototypes of reactors according to some embodiments of the present invention.

FIG. 3 is a digital image of two prototypes of continuous sono-chemical reactors according to some embodiments of the present invention. The first prototype (left) was made with Nylatron, a sound absorbing material, and included a separation section. The second prototype (right) was made with Nylatron further coated with aluminum powder, which is sound reflecting material. In addition, the second prototype included the separation section. Each of the prototypes of the reactors has a volume of 0.9 liters.

The two prototypes have three sections, the top converging section where the sonotrode is placed, the central section where the static mixer is housed and the bottom separation section including outlets. The converging section allows for a pseudo ultrasonic flow cell type construction, which promotes the use of low power ultrasound sources. The static mixer section allows for non-energy consuming conversion process. The bottom section enables the separation and draining products and/or byproducts to occur. The height of the reactors is 40 cm, the diameter converges from 10 cm in the top most section to 2.5 cm at the bottom most section over the height. The diameter remains constant throughout the static mixer section and converges at the bottom of the separation section. This small convergence allows for phase separation between the produced biodiesel and byproduct glycerol. Inlets are provided at the top and can either be single or multiple. Outlets are at the bottom. Depending on the sonotrode size and the applied power and frequency, the maximum inlet flow rate can be in a range of about 10-50 l/hr. An assay of the physics involved in the entire process, using numerical simulation tools has been the criteria for evaluating the reactor design.

Example 1. Pretreatment of Waste Oils or Other Oils

Prior to being supplied into the reactor, the mixture of the reactants was pretreated for higher conversion rates and better quality biodiesel. The pretreatment methods include some or all of the following: filtering of oil (e.g., using a mesh with about 20 μm openings), heating of oil for moisture extraction/release, and dissolution of catalyst in alcohol to produce a homogeneous blend of alkoxide. Methanol ($CH_3OH$) or ethanol ($C_2H_5OH$) are commonly used alcohols. Sodium hydroxide (NaOH) or potassium hydroxide (KOH) have been commonly used as the catalyst.

Figure 4A:
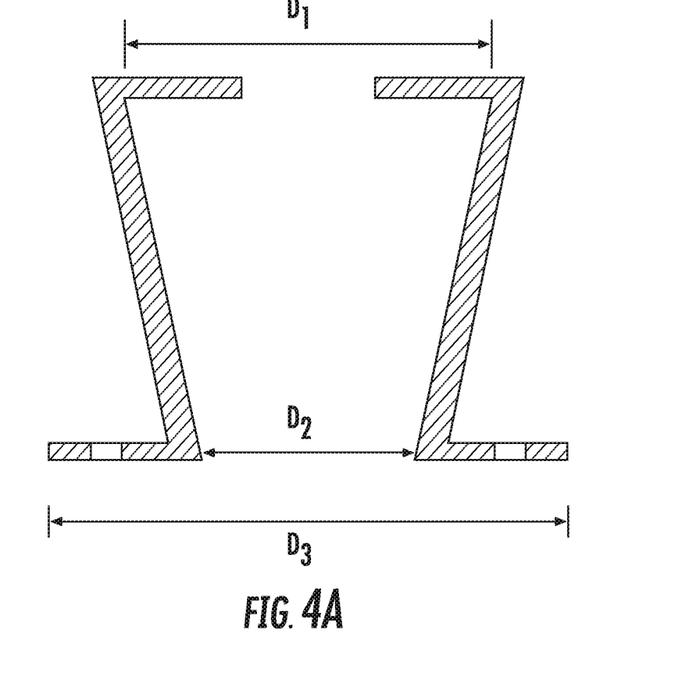
Figure 4B:
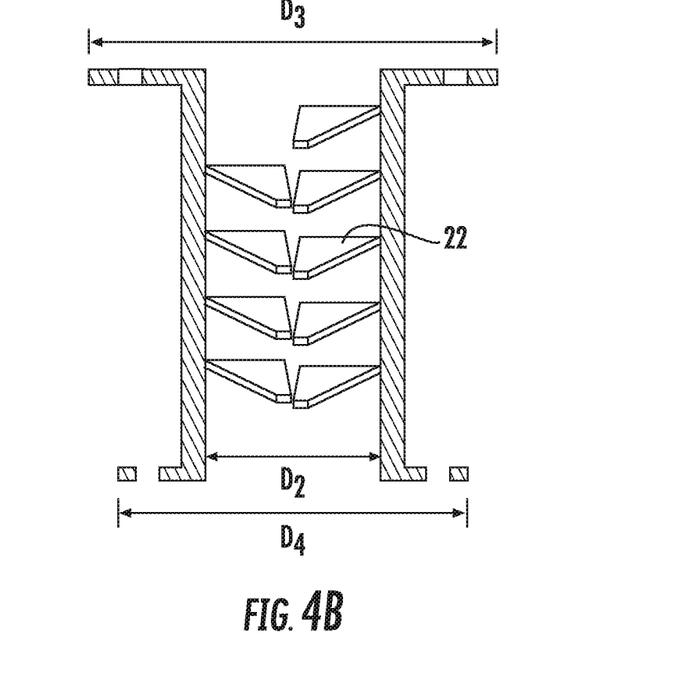
Figure 4C:
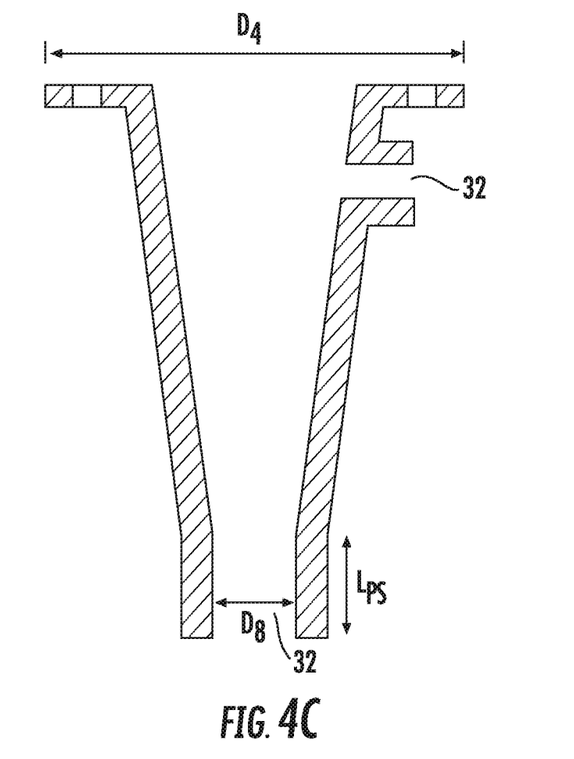
Figure 4D:
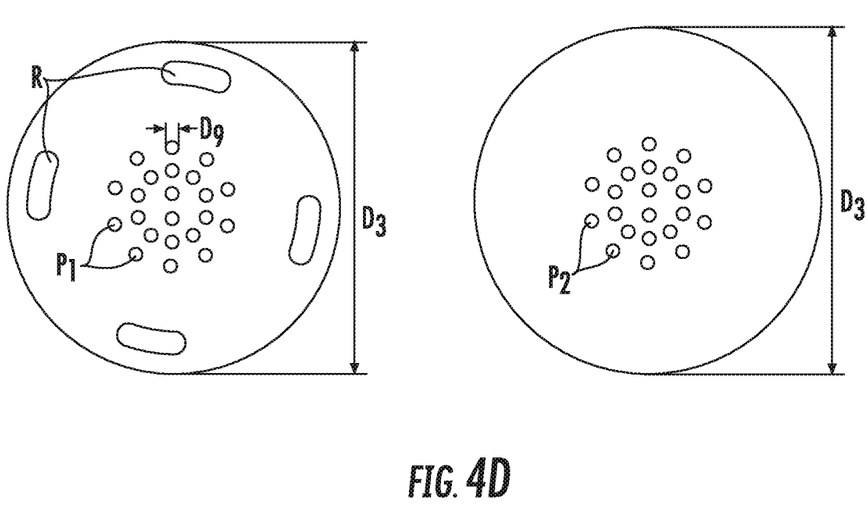
FIG. 4D is a plan view of sections of a sono-chemical reactor according to some embodiments of the present invention.

FIGS. 4A, 4B, and 4C are cross-sectional views and FIG. 4D is a plan view of sections of a sono-chemical reactor according to some embodiments of the present invention, which will be discussed as Examples below.

Example 2. Converging Section

The top section (i.e., the sono-reactor section 10) has a shape of a converging cylinder, and this shape allows for acoustic energy concentration and provides more energy per unit volume than a generic cylindrical design. The top section operates as a pseudo-flow cell, and therefore expensive flow cells may not be needed. FIG. 4A is a cross-sectional view of the top section (i.e., the sono-reactor section 10). Referring to FIG. 4A, an uppermost end of an inner space of the top section has a first diameter D1 and a lowermost end of the inner space of the top section may has a second diameter D2. In some embodiments, the diameter of the inner space of the top section may be gradually decrease from the first diameter D1 to the second diameter D2, as illustrated in FIG. 4A. A bottom portion of the top section, which is connected to a lower section, has a third diameter D3. For example, D1 is about 116 mm, D2 is about 60 mm, and D3 is about 140 mm.

After a brief premixing of oil and alkoxide, the fluid mixture was fed into the reactor (left) shown in FIG. 3 through two inlets at a flow rate of 0.9 liters/hr. In some embodiments, more than two inlets can be used. Flow rates can vary from about 10 liters to about 50 liters per hour. At least two inlets are provided in the prototype reactor to allow separate streams of oil and methanol. A peristaltic pump can be used to control the flow rate to be suitable for sonication. The ultrasonic equipment used is Hielscher UP-400S that has maximum power of 400 W and a frequency of 24 KHz. Multiple power settings are facilitated in this equipment. The option of using the multiple sonotrodes at multiple modes such as pulse and continuous is also available.

The inlet flow rate depends on the sonotrode size, frequency and applied power. Ultrasonic equipments with a frequency range of 20-70 KHz and power range of 100-1200 W are commonly applied. It should be noted that commercial flow cells do not allow a big range of sonotrode usage. Specifically, a big range of size of sonotrode may not used with commercial flow cells. On the contrary, the reactors according to some embodiments of the present invention allow use of sonotrodes of any size. As the mixture enters the reactor and flows through the converging top section, it comes in contact with the sonotrode. For example, the sonotrode is a stack of piezo-electric transducers that amplifies the frequency of ultrasound into the fluid. The high frequency pressure waves from the sonotrode create cycles of compressions and rarefactions, creating a cloud of cavitation voids or bubbles in the mixture. The pressure and temperature within these bubbles can reach enormous levels (e.g., 1000 atm, 5000 K). As the acoustic pressure exceeds certain threshold pressure of the bubbles, the bubbles may implode. Implosion of these bubbles may cause several effects, for example, shockwaves, radical formation, intense localized mixing etc. This whole development takes place in a matter of seconds.

The combination of such effects along with the high localized physical conditions may increase reaction rate. Even though the bubble cloud favors reaction propagation, it also acts as a hindrance to the pressure waves, causing attenuation of the wave. This effect of the bubbles curbs the opportunity of increasing the reactor size. The compactness of the reactor has to be maintained so as to concentrate the ultrasound energy to a small volume and to avoid energy loss due to attenuation. The fluid mixture undergoes this process in the convergent chamber. The converging design helps in further concentrating the sonic energy as the mixture flows out of this section.

Example 3. Static Mixer Section

The mixture leaving the converging section still contains some unreacted substances, free radicals from the implosion of bubbles, and reacting substances. Previously developed sono-chemical reactors simply discharged this mixture as the product. According to some embodiments of the present invention, a static mixer section is connected to the converging section. A static mixer is a passive device and does not require any energy input, and the static mixer moves the reaction forward by creating supplementary agitation.

In this new design, the residual mixture is further processed as residual mixture passes through a static mixer in the center section. The central, narrower static mixer section is a unique feature that allows for further processing of unreacted chemicals passively. FIG. 4B is a cross-sectional view of the static mixer section. Referring to FIG. 4B, an inner space of the static mixer section has a substantially uniform diameter along the longitudinal direction of the reactor and has the second diameter D2. The top end of the static mixer section that is connected to an upper section may have the third diameter D3, and the bottom end of the static mixer section that is connected to a lower section may have a fourth diameter D4. For example, the fourth diameter D4 is about 120 mm. The static mixer section includes blades 22 of a static mixer.

A static mixer allows for maximized usage of the reactor space, and the design allows for using interchangeable and different static mixers that includes, for example, a conventional helical screw type or innovative staggered desiccated type. The staggered desiccated mixer is indigenously designed to give a good balance between flow rate and mixing. Further, the static mixer consists of a series of blades of any shapes and any sizes depending on the viscosity of the fluid, such as helical channel, circular ladder or simple staggered chevrons. Various static mixers can be used depending the viscosity and velocity of the fluid.

Figure 5A:
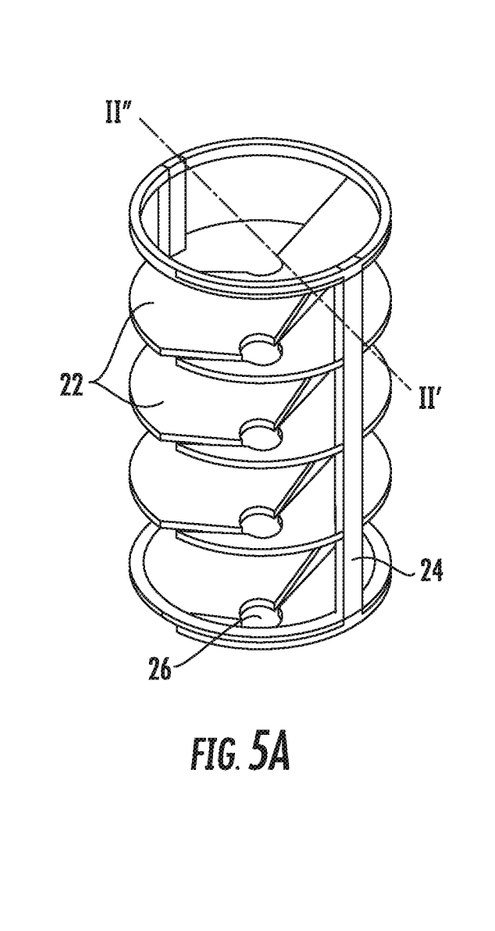
FIG. 5A is a perspective view of a stepped static mixer of a static mixer section according to some embodiments of the present invention.
Figure 5B:
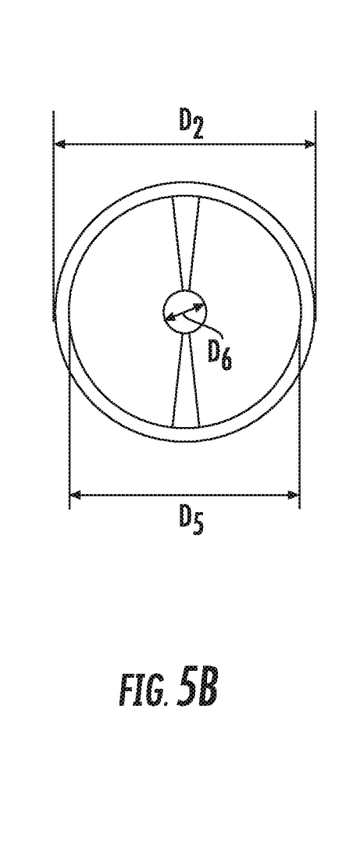
FIGS. 5B and 5C are a plan view and a cross-sectional view of the stepped static mixer of FIG. 5A, respectively.
Figure 5C:
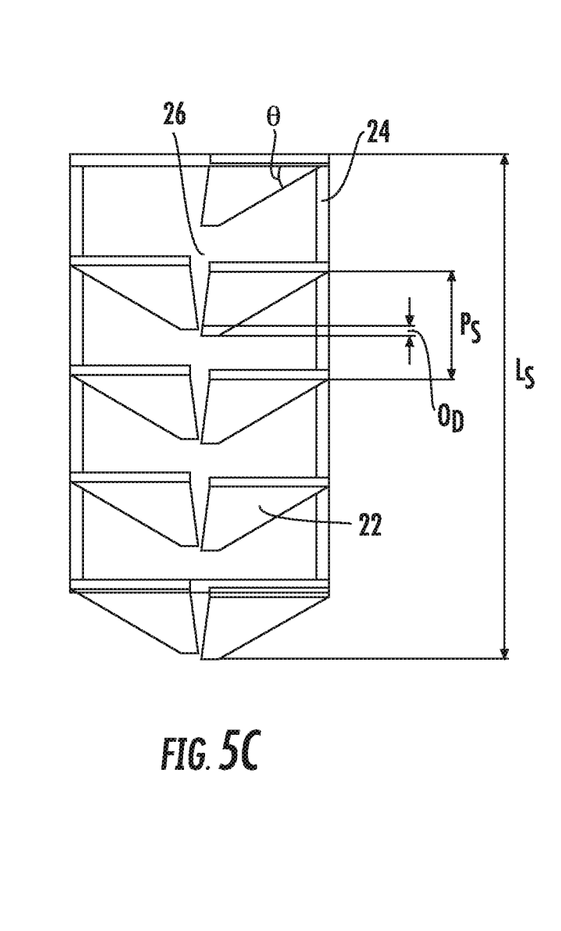

FIG. 5A is a perspective view of a stepped static mixer of the static mixer section according to some embodiments of the present invention, and FIGS. 5B and 5C are a plan view and a cross-sectional view of the stepped static mixer of FIG. 5A, respectively. Referring to FIG. 5A, the stepped static mixer may include blades 22 and a frame 24 to which the blades 22 are attached. Referring to FIG. 5B, the blades 22 may have a fifth diameter, the frame 24 may have the second diameter D2, and a central opening 26 may have a sixth diameter D6. For example, the fifth diameter D5 is about 54 mm, and the sixth diameter D6 is about 5 mm.

Referring to FIG. 5C, at the entrance of the stepped static mixer, the fluid may flow on the inclined blade 22, and an inclined angle θ may be, for example, 30°. A high inclined angle θ may allow for processing high viscosity fluid. The stepped static mixer has a length Ls in the longitudinal direction of the reactor, which is about 115 mm (e.g., 116.43 mm). Two blades may be spaced apart from each other in the vertical direction by a distance Ps (e.g., about 25 mm). Two blades 22, which are spaced part in the horizontal direction, may be offset in the longitudinal direction of the reactor by a distance OD, which is about 2 mm (e.g., 1.68 mm). The distance Ps and/or the distance OD may be increased or decreased to increase or decrease the mixing rate. Additionally, the number of the blades 22 may be changed.

Figure 6A:
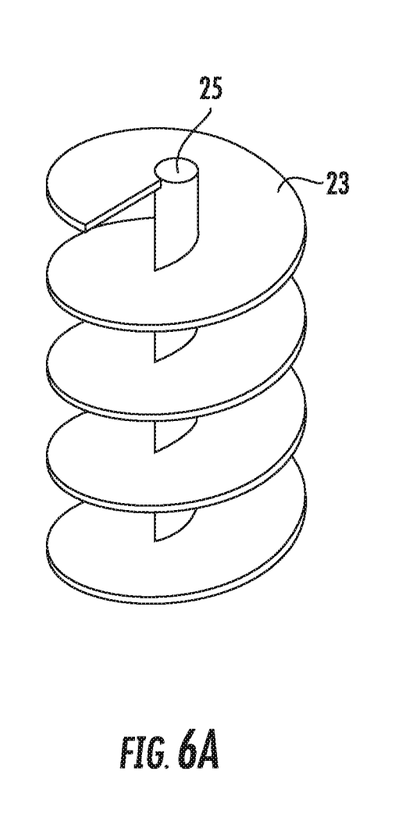
FIG. 6A is a perspective view of a helical blade of the static mixer section according to some embodiments of the present invention.
Figure 6B:
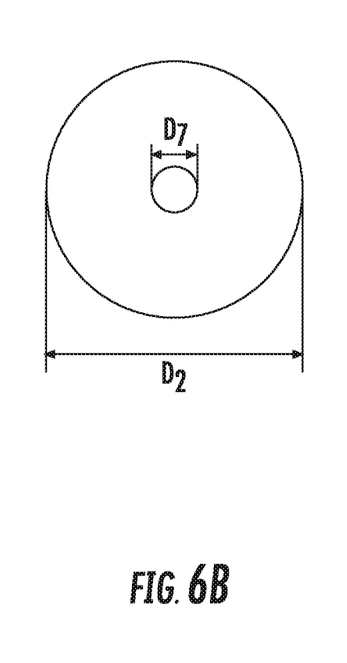
FIGS. 6B and 6C are a plan view and a front view of the helical blade of FIG. 6A, respectively.
Figure 6C:
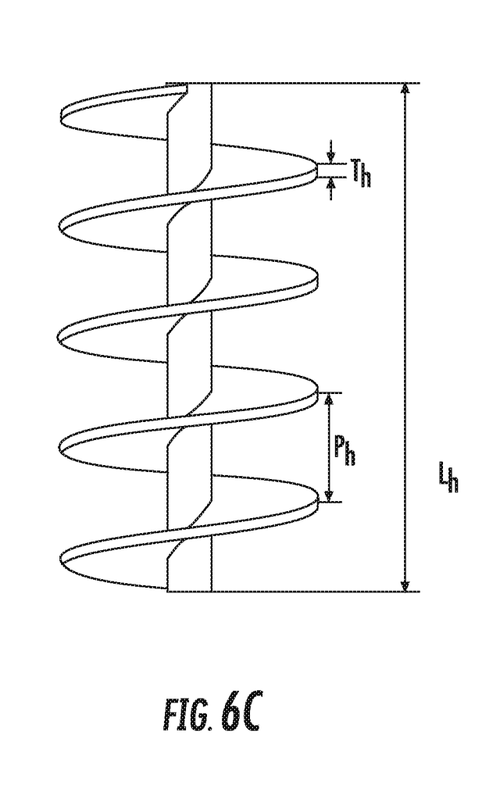

FIG. 6A is a perspective view of a helical blade of the static mixer section according to some embodiments of the present invention, and FIGS. 6B and 6C are a plan view and a front view of the helical blade of FIG. 6A, respectively. A static mixer section including a helical blade (i.e., a helical mixer) may provide high flow rate but relatively lower mixing. The helical mixer may be used to process lower viscosity fluid. Referring to FIG. 6B, the helical blade 23 may have the second diameter D2 and a core 25 of the helical blade 23 may have a seventh diameter D7. For example, the seventh diameter D7 is about 5 mm. Referring to FIG. 6C, the helical blade 23 has a length Lh and, for example, the length Lh is about 115 mm (e.g., 114.48 mm). The helical blade 23 may have a thickness Th of about 2 mm, a pitch Ph of about 25 mm, and 4.5 revolutions. The start angle of the helical blade 23 may be about 0 degree. It will be understood that properties of a fluid to be processed may vary, and thus the thickness, the pitch and revolutions of the helical blade may be changed accordingly.

While the mixture passes through the static mixer, the interaction between the reactants increases and the reaction proceeds. The static mixer can be made of any chemically inert and soft materials like plastic or a harder metal (e.g., mild steel and alloys). This reactor design facilitates commutative action of the static mixer that suits the viscosity of the fluid. The static mixer blades may section the top and middle regions in a way that the residence time in the top-convergent region may be increased.

Example 4: Separation Section

FIG. 4C is a cross-sectional view of the separation section. Locations of outlets 32 may allow for separation of the biodiesel and glycerol by gravity. Each of the outlets 32 may be connected to one valve. Glycerol that settles at the bottom may be discharged through the outlet 32 adjacent a bottom portion of the separation section, and biodiesel that settles above the glycerol may be discharged through the outlet 32 adjacent a top portion of the separation section. By allowing the residual glycerol to be partially extracted and/or separated from the mixture, the reverse reaction may be reduced or possibly suppressed.

In some embodiments, an inner space of the separation section may taper along the longitudinal direction of the reactor away from the static mixer section, as illustrated in FIG. 4C. This shape may allow for separation of products, and the double outlets 32 and valves may facilitate removal of glycerol thereby possibly suppressing reverse reaction. A top portion of the separation section that is connected to an upper section (e.g., the static mixer section) may have a fourth diameter D4 of about 120 mm. An uppermost portion of the inner space of the separation section may have a second diameter D2 of about 60 mm and a lowermost portion of the inner space of the separation section has a eighth diameter D8 of about 50 mm. In some embodiments, a lower portion of the inner space of the separation section has a substantially uniform diameter and a length Lps of the lower portion is about 30 mm.

Example 5. Controlling Disk Section

FIG. 4D shows plan views of first and second controlling disks 42 and 44 of the controlling disk section 40. The first controlling disk 42 may include first perforations P1, and the second controlling disk 44 may include second perforations P2. The first and second controlling disks 42 and 44 may control flow of the fluid from an upper section (e.g., the sono-reactor section 10) into a lower section (e.g., the static mixer section 20) by changing alignment between the first perforations P1 and the second perforations P2. The alignment between the first perforations P1 and the second perforations P2 may be changed by rotating one of the first and second controlling disks 42 and 44. Rotating angle can be controlled using openings R of the first controlling disk 42. For example, each of the first perforations P1 and the second perforations P2 has a ninth diameter D9 of about 6 mm. Although FIG. 4D shows two controlling disks, more than two controlling disks can be used.

All sections of the reactor may be manufactured separately and assembled later to keep its manufacturing, maintenance and replacement simple. All the sections of the reactor may be joined by flange as illustrated in FIG. 2. The reactor can be manufactured using Teflon or metal (e.g., steel and aluminum).

Example 6. Simulations

To analyze the physics involved in the complete reactor operation, heuristic numerical simulation of each of the physics is carried out. The design was evaluated by analyzing the acoustic wave propagation, reactant flow and chemical kinetics.

Figure 7:
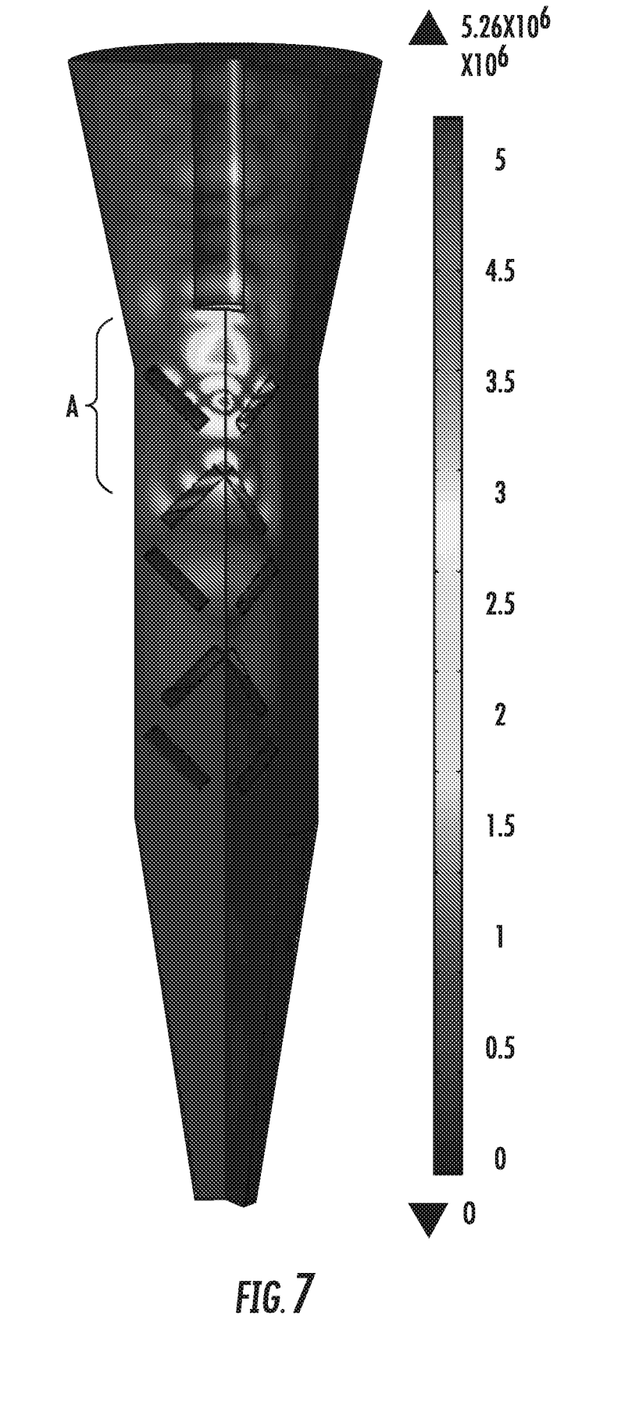
FIG. 7 illustrates the acoustic pressure amplitude (Pa) when a sono-chemical reactor is operating.

The acoustic wave was simulated by solving the Helmholtz equation, modified to include the wave attenuation due to cavitation bubble cloud. FIG. 7 illustrates the acoustic pressure amplitude (Pa). Referring to FIG. 7, the acoustic pressure is higher in a portion A of the reactor, which is adjacent an entrance of the static mixer section 20, and the acoustic pressure in the portion A is about from $3 \times 10^6$ Pa to about $4 \times 10^6$ Pa.

Vegetable oil and methanol are two immiscible fluids, but in a premixed state the solution can be assumed to have a uniform mixing of these two fluids in the reactor. Secondly, ultrasonic cavitation causes undulations in the flow profile due to shockwaves and pressure variations. However, this model is a linear approximation hence does not integrate such effects. Considering these assumptions, the laminar, 2D, incompressible, viscous Navier Stokes equations is used to simulate the flow of reactants inside the reactor.

Figure 8:
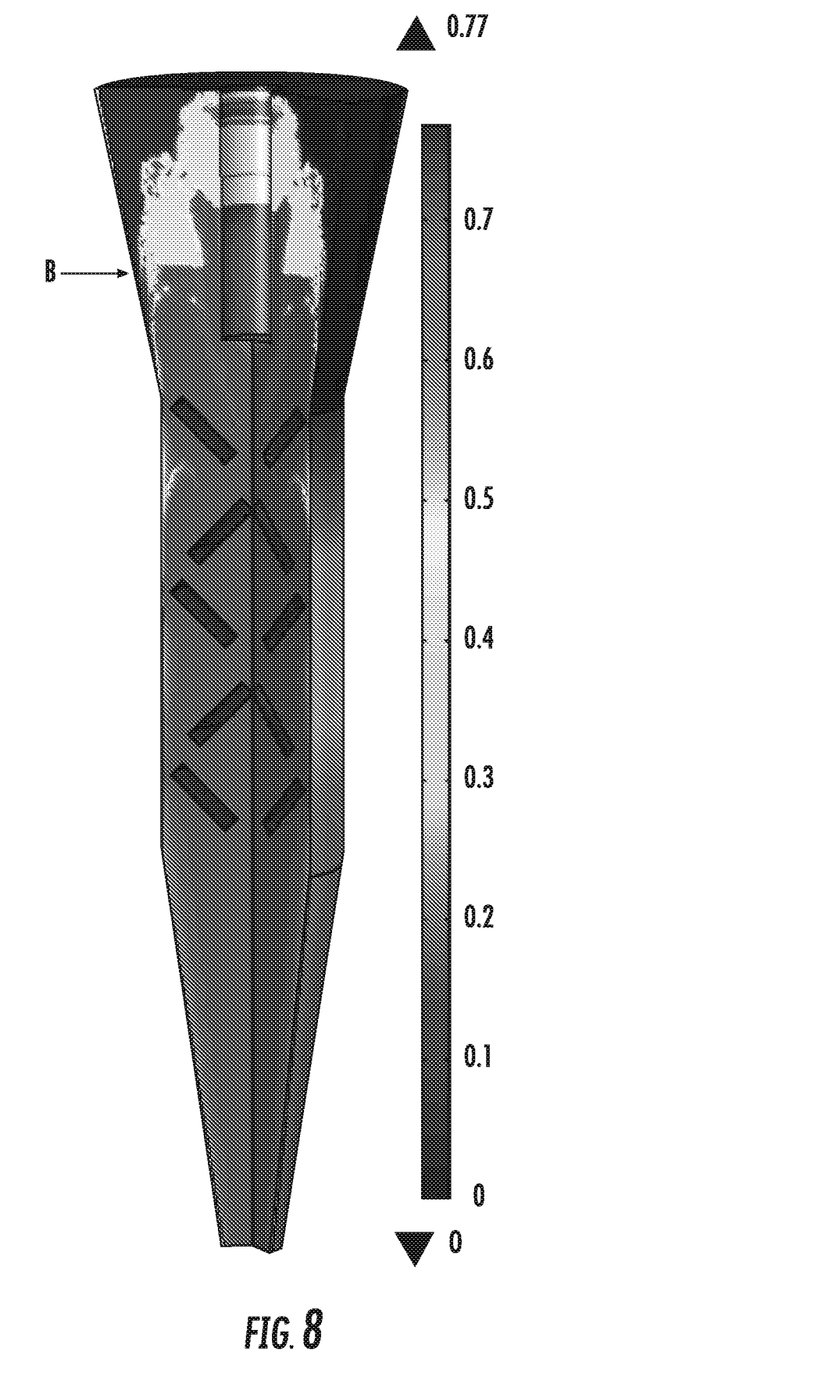
FIG. 8 illustrates a change of a biodiesel mole-fraction obtained using a reactive flow simulation.

FIG. 8 shows biodiesel mole-fraction obtained using reactive flow simulation. Interaction between reactants occurring due to the flow of reactant mixture in the reactor promotes increase in transesterification. The reactor was designed in a way that the flow is highly efficient in promulgating the reaction, such that high yields of biodiesel are attained even in absence of sonication. To analyze this aspect of the reactor, species transport equation is used to predict the resulting biodiesel concentrations within the reactor. Four species, vegetable oil, methanol, FAME (biodiesel) and glycerol are transported through the reactor. As illustrated in FIG. 8, the biodiesel mole-fraction is substantially uniform in a lower portion of the reactor that is disposed below the line B, and the biodiesel mole-fraction in the lower portion of the reactor is about or greater than 0.7.

The reaction is defined by the Arrhenius kinetics model, the most defining part in evaluating the design of the reactor is the total reaction rate of biodiesel formation. This is used as the judging factor for the reactor design. The total reaction rate is the logical sum of the reaction rate due to sonication and reaction rate due to reacting flow. The kinetic rate coupling model is used to quantify and sum the individual reaction rates. Only thermal effect of sonication is incorporated in this model. The temperature inside the cavitation bubble is modelled as a function of the acoustic pressure assuming the vapor inside the bubble to be a molar mixture of oil and methanol vapors. The Arrhenius model is then applied to find the rate constant of sonication. As the physical phenomena suggests that the reaction rate due to sonication comes in to effect only with the implosion of cavitation bubble, the rate of reaction has to be a function of the cavitation bubble volume. But since the bubble implodes only when the acoustic pressure is greater than the Blake threshold pressure, the sonication reaction rate equation comes into account only when P>Pblake.

The above-disclosed subject matter is to be considered illustrative, and not restrictive, and the appended claims are intended to cover all such modifications, enhancements, and other embodiments, which fall within the true spirit and scope of the inventive concept. Thus, to the maximum extent allowed by law, the scope is to be determined by the broadest permissible interpretation of the following claims and their equivalents, and shall not be restricted or limited by the foregoing detailed description.

Which is claimed is:

1. A sono-chemical reactor comprising:
    a plurality of sections that are sequentially connected along a longitudinal direction of the sono-chemical reactor,
    wherein the plurality of sections comprises:
    a sono-reactor section that comprises a reactant inlet through which reactants are supplied into the sono-reactor section, wherein an inner space of the sono-reactor section tapers along the longitudinal direction of the sono-chemical reactor away from the reactant inlet; and
    a static mixer section that is configured to receive a first reactant/product mixture from the sono-reactor section and is configured mix the first reactant/product mixture therein for reaction between unreacted reactants,
    wherein an inner space of the static mixer section has a substantially uniform diameter along the longitudinal direction of the sono-chemical reactor, and
    wherein the diameter of the inner space of the static mixer section is substantially equal to a smallest diameter of the inner space of the sono-reactor section.

2. The sono-chemical reactor of claim 1, further comprising a first controlling disk and a second controlling disk that are disposed between the sono-reactor section and the static mixer section,
    wherein the first controlling disk comprises a plurality of first perforations, and the second controlling disk comprises a plurality of second perforations, and
    wherein the first and second controlling disks are configured to control flow of the first reactant/product mixture from the sono-reactor section into the static mixer section by changing alignment between the plurality of first perforations and the plurality of second perforations.

3. The sono-chemical reactor of claim 1, wherein the plurality of sections further comprise a product separation section that is configured to receive a second reactant/product mixture from the static mixer section and is configured to separate a product from the second reactant/product mixture.

4. The sono-chemical reactor of claim 3, wherein an inner space of the product separation section tapers along the longitudinal direction of the sono-chemical reactor away from the static mixer section.

5. The sono-chemical reactor of claim 4, wherein the product separation section comprises two outlets that are spaced apart from each other in the longitudinal direction of the sono-chemical reactor.

6. The sono-chemical reactor of claim 1, wherein a ratio of a largest diameter of the inner space of the sono-reactor section to a smallest diameter of the inner space of the sono-reactor section in the traverse direction is about 10:6.

7. A method of producing biodiesel using the sono-chemical reactor of claim 1, wherein the method comprises continuously supplying the reactants into the sono-chemical reactor and discharging a product from the sono-chemical reactor.

8. The method of claim 7, wherein the plurality of sections are vertically stacked on each other.

9. A sono-chemical reactor comprising:
    a sono-reactor section that comprises a reactant inlet through which reactants are supplied into the sono-reactor section;
    a static mixer section that is configured to receive a first reactant/product mixture from the sono-reactor section and is configured to mix the first reactant/product mixture therein for reaction between unreacted reactants, wherein the sono-reactor section and the static mixer section are connected to each other in a longitudinal direction of the sono-chemical reactor;
    a product separation section that is configured to receive a second reactant/product mixture from the static mixer section and is configured to separate a product from the second reactant/product mixture, wherein the product separation section comprises two outlets that are spaced apart from each other in the longitudinal direction of the sono-chemical reactor; and a first controlling disk and a second controlling disk that are disposed between the sono-reactor section and the static mixer section, wherein the first controlling disk comprises a plurality of first perforations, and the second controlling disk comprises a plurality of second perforations, and wherein the first and second controlling disks are configured to control flow of the first reactant/product mixture from the sono-reactor section into the static mixer section by changing alignment between the plurality of first perforations and the plurality of second perforations.

10. The sono-chemical reactor of claim 9, wherein an inner space of the static mixer section has a substantially uniform diameter along the longitudinal direction of the sono-chemical reactor, and wherein the diameter of the inner space of the static mixer section is less than a largest diameter of an inner space of the sono-reactor section.

11. The sono-chemical reactor of claim 9, wherein an inner space of the sono-reactor section tapers along the longitudinal direction of the sono-chemical reactor away from the inlet.

12. The sono-chemical reactor of claim 9, wherein an inner space of the product separation section tapers along the longitudinal direction of the sono-chemical reactor away from the static mixer section.

13. A method of producing biodiesel using the sono-chemical reactor of claim 9, wherein the method comprises continuously supplying the reactants into the sono-chemical reactor and discharging a product from the sono-chemical reactor.

14. The method of claim 13, wherein the sono-reactor section and the static mixer section are vertically stacked.

* * * * *